United States Patent
Zhang

(10) Patent No.: US 10,327,648 B2
(45) Date of Patent: Jun. 25, 2019

(54) BLOOD VESSEL MECHANICAL SIGNAL ANALYSIS

(71) Applicant: Siemens Medical Solutions USA, Inc., Malvern, PA (US)

(72) Inventor: Hongxuan Zhang, Palatine, IL (US)

(73) Assignee: Siemens Healthcare GmbH, Erlangen (DE)

( * ) Notice: Subject to any disclaimer, the term of this patent is extended or adjusted under 35 U.S.C. 154(b) by 184 days.

(21) Appl. No.: 14/676,539

(22) Filed: Apr. 1, 2015

(65) Prior Publication Data

US 2016/0287092 A1    Oct. 6, 2016

(51) Int. Cl.
| | |
|---|---|
| A61B 5/00 | (2006.01) |
| A61B 5/02 | (2006.01) |
| A61B 7/04 | (2006.01) |
| A61B 5/026 | (2006.01) |
| A61B 5/0205 | (2006.01) |
| A61B 5/1455 | (2006.01) |

(52) U.S. Cl.
CPC ........ *A61B 5/02007* (2013.01); *A61B 5/0205* (2013.01); *A61B 5/026* (2013.01); *A61B 5/14551* (2013.01); *A61B 5/6824* (2013.01); *A61B 5/7275* (2013.01); *A61B 5/746* (2013.01); *A61B 7/04* (2013.01)

(58) Field of Classification Search
CPC ............ A61B 2017/0011; A61B 5/026; A61B 5/6824; A61B 5/02007
See application file for complete search history.

(56) References Cited

U.S. PATENT DOCUMENTS

| | | | |
|---|---|---|---|
| 4,549,552 A | 10/1985 | Groch et al. | |
| 5,139,026 A | 8/1992 | Niwa | |
| 5,700,283 A | 12/1997 | Salo | |
| 5,792,195 A | 8/1998 | Carlson et al. | |
| 5,906,582 A | 5/1999 | Kondo et al. | |
| 6,080,111 A | 6/2000 | Pao-Lang | |
| 6,368,283 B1 | 4/2002 | Xu et al. | |
| 6,491,647 B1 * | 12/2002 | Bridger | A61B 5/021 128/900 |
| 6,527,729 B1 * | 3/2003 | Turcott | A61B 5/0002 600/528 |
| 6,643,548 B1 | 11/2003 | Mai et al. | |
| 6,650,940 B1 | 11/2003 | Zu et al. | |
| 6,721,386 B2 | 4/2004 | Bulkes et al. | |
| 7,048,697 B1 | 5/2006 | Mitsuru | |
| 7,079,896 B1 | 7/2006 | Park et al. | |

(Continued)

FOREIGN PATENT DOCUMENTS

WO    WO 9518564 A1 *   7/1995    ......... A61B 5/02007

*Primary Examiner* — Lynsey C Eiseman
*Assistant Examiner* — Amanda L Steinberg

(57) ABSTRACT

Disclosed herein is a framework for facilitating patient signal analysis. In accordance with one aspect, the framework receives signal data including mechanical signal data, wherein the mechanical signal data is generated in response to mechanical contraction of blood vessels. A region of interest is segmented from the mechanical signal data. One or more mechanical signal ratios may be determined based on parameters extracted from the segmented region of interest to characterize waveform changes. A report may then be generated based at least in part on the one or more mechanical signal ratios.

19 Claims, 7 Drawing Sheets

(56) References Cited

U.S. PATENT DOCUMENTS

| | | |
|---|---|---|
| 7,226,418 B2 | 6/2007 | Kim |
| 7,326,180 B2 | 2/2008 | Tanabe et al. |
| 7,347,823 B2 | 3/2008 | Yeh |
| 7,526,332 B2 | 4/2009 | Amano et al. |
| 7,527,597 B2 | 5/2009 | Sandler et al. |
| 7,953,484 B2 | 5/2011 | Brockway et al. |
| 8,025,624 B2 | 9/2011 | Wariar et al. |
| 8,036,301 B2 | 10/2011 | Cho et al. |
| 8,041,424 B2 | 10/2011 | Corbucci |
| 8,133,187 B2 | 3/2012 | Holmstrom et al. |
| 8,185,190 B2 | 5/2012 | Bauer et al. |
| 8,235,912 B2 | 8/2012 | Schmidt et al. |
| 8,317,716 B2 | 11/2012 | Lee et al. |
| 8,419,649 B2 | 4/2013 | Banet et al. |
| 8,452,398 B2 | 5/2013 | Libbus et al. |
| 8,494,631 B2 | 7/2013 | Zhang et al. |
| 8,500,650 B2 | 8/2013 | Siejko et al. |
| 8,545,416 B1 * | 10/2013 | Kayyali ............... A61B 5/085 128/204.23 |
| 8,548,588 B1 | 10/2013 | Bauer |
| 8,554,313 B2 | 10/2013 | Giorgis et al. |
| 8,579,828 B2 | 11/2013 | Carlson et al. |
| 8,636,669 B2 | 1/2014 | Siejko et al. |
| 8,647,283 B2 | 2/2014 | Matsumoto et al. |
| 8,682,428 B2 | 3/2014 | Holmstrom et al. |
| 8,690,788 B2 | 4/2014 | Ide et al. |
| 8,734,358 B1 | 5/2014 | Criley et al. |
| 2006/0022833 A1 * | 2/2006 | Ferguson ............. A61B 5/1126 340/573.1 |
| 2008/0177191 A1 * | 7/2008 | Patangay ............ A61B 5/0402 600/509 |

* cited by examiner

Note: for pulse sound signal, $Uni\_time\_energy\_integration\_ratio_{sound}(N)$ was used; for vibration signal, $Uni\_time\_energy\_integration\_ratio_{vibration}(M)$ was used.

BLOOD VESSEL MECHANICAL SIGNAL ANALYSIS

TECHNICAL FIELD

The present disclosure generally relates to systems and methods for blood vessel mechanical signal analysis.

BACKGROUND

The most frequent killer of Americans is cardiovascular disease. Cardiac pathology, such as atrial fibrillation and myocardial ischemia (MI), may be diagnosed by using cardiac electrophysiological (EP) signals and hemodynamic signals (e.g., invasive blood pressure signals). Cardiac arrhythmia detection is typically performed using surface electrocardiogram (ECG) signal, intra-cardiac EP signal and hemodynamic signal analyses based on waveform morphology and time domain parameters.

Currently, known non-invasive clinical methods rely mainly on surface ECG, peripheral capillary oxygen saturation (SPO2), non-invasive blood pressure (NIBP), respiration and temperature signal analysis to determine electrophysiological characteristics and hemodynamic parameters, oximetric blood content, max-min pressure resonance, capnographic and temperature changes information, etc. for monitoring. However, such information does not fully utilize circulation information, such as blood propagation and vibration patterns, vessel wall vibration sound mode, etc.

Most known clinical blood function analyses still rely on catheter technologies (e.g., intra-cardiac blood pressure catheter, Swan-Ganz catheter, etc.), and are usually invasive or partially invasive. In most clinical methods for cardiac signal monitoring, the sensors are active and usually send detecting signals (e.g., ultrasound signal, stimulation signal, etc.) to patient tissue and receive feedback and response signals (e.g., alternating current or AC impedance measurement) for comparison and function diagnosis. These sensors are usually invasive and add unnecessary regulatory and patient safety risk due to, for example, leakage current.

Known methods for cardiac arrhythmia detection focus on qualitative pathology characterization and quantification based on signal time domain amplitude (e.g., ST segmentation elevation in surface ECG signals). Recently, some studies have applied new algorithms for cardiac arrhythmia detection, such as frequency domain parameter, time-frequency distribution mapping, statistical entropy, etc. However, these algorithms typically fail to take into consideration mechanical vibration and sound waveform data associated with the patient's body, which can be useful in quantifying cardiac function.

SUMMARY

The present disclosure relates to a framework for facilitating patient signal analysis. In accordance with one aspect, the framework receives signal data including mechanical signal data, wherein the mechanical signal data is generated in response to mechanical contraction of blood vessels. A region of interest is segmented from the mechanical signal data. One or more mechanical signal ratios may be determined based on parameters extracted from the segmented region of interest to characterize waveform changes. A report may then be generated based at least in part on the one or more mechanical signal ratios.

This summary is provided to introduce a selection of concepts in a simplified form that are further described below in the following detailed description. It is not intended to identify features or essential features of the claimed subject matter, nor is it intended that it be used to limit the scope of the claimed subject matter. Furthermore, the claimed subject matter is not limited to implementations that solve any or all disadvantages noted in any part of this disclosure.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings. Furthermore, it should be noted that the same numbers are used throughout the drawings to reference like elements and features.

DETAILED DESCRIPTION

Figure 1:
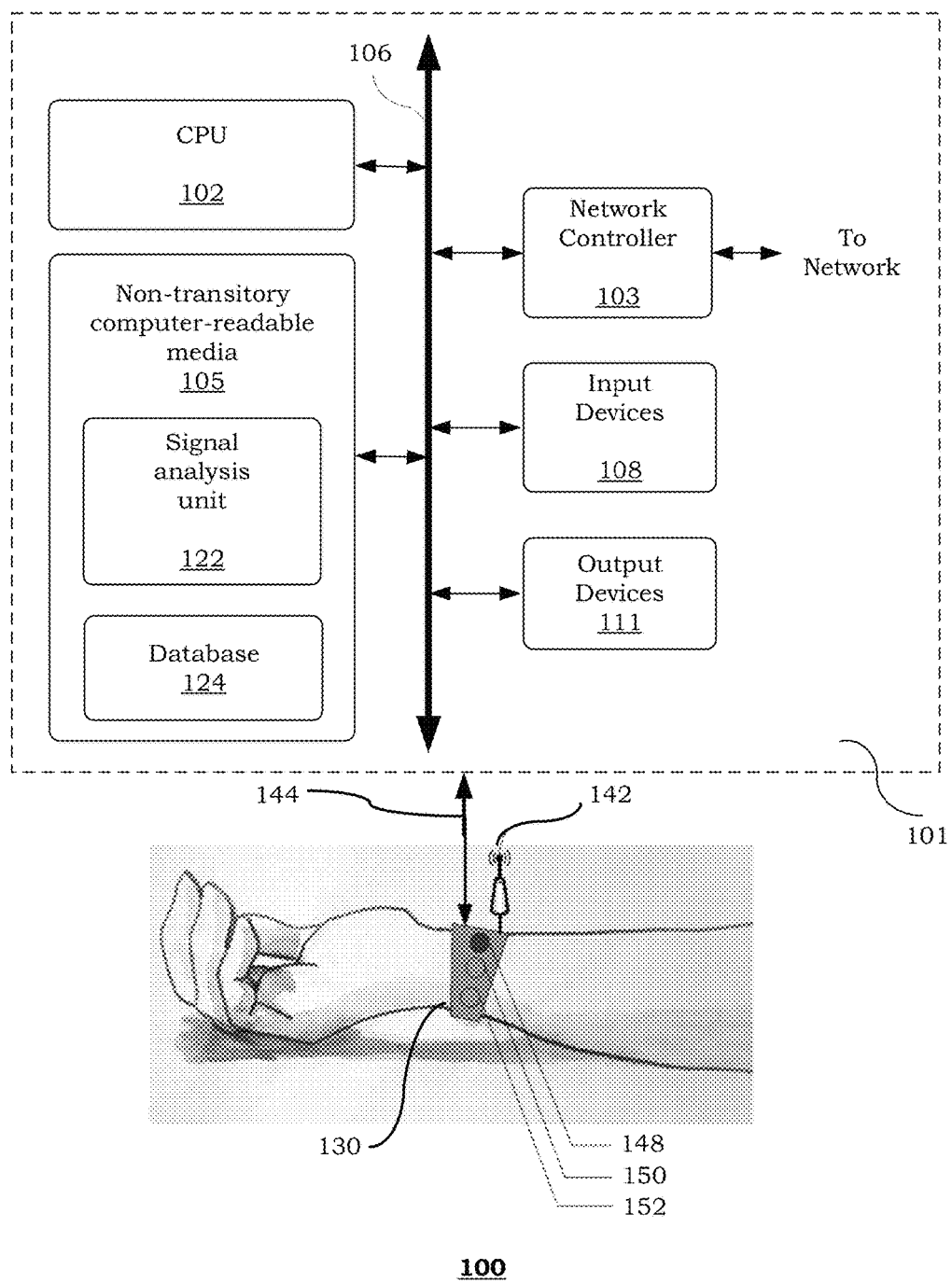
FIG. 1 shows an exemplary system.

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. While the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

It is to be understood that the system and methods described herein may be implemented in various forms of hardware, software, firmware, special purpose processors, or a combination thereof. Preferably, the present invention is implemented in software as an application (e.g., n-tier application) comprising program instructions that are tangibly embodied on one or more program storage devices (e.g., magnetic floppy disk, RAM, CD ROM, ROM, etc.), and executable by any device or machine comprising suitable architecture. If written in a programming language conforming to a recognized standard, sequences of instructions designed to implement the methods can be compiled for execution on a variety of hardware platforms and for interface to a variety of operating systems. In addition, embodiments of the present framework are not described with reference to any particular programming language. It will be appreciated that a variety of programming languages may be used to implement embodiments of the present invention.

The cardiac cycle is usually generated by contraction and reperfusion of the heart, during which the heart contracts via systole, pushing blood out of the heart, and relaxes via diastole, filling the heart with blood. This creates alternate expansion and contraction of the artery walls while heart action varies blood volume within the arteries. Artery walls are elastic. Hence, they become distended by increased blood volume during systole (or contraction of the heart). During diastole (or relaxation of the heart), blood volume in the arteries decreases and the walls contract, propelling the blood farther along the arterial pathway. A propagation wave is initiated by the heartbeat and travels from the aorta (major artery leaving the heart) along the walls of other arteries. The mechanical vibration of the artery walls caused by the pulse propagation can be sensed and acquired at different parts of the patient's body that are remote from the heart, such as a peripheral artery (e.g., radial artery at the wrist), to diagnose cardiac tissue malfunctions, especially cardiac arrhythmia. However, there are currently no reliable methods for categorizing mechanical characteristics of blood flow based upon heart tissue analysis for deriving cardiac pathology information, especially for non-symptomatic cardiac arrhythmias and prediction of secondary injury of the heart and circulation system.

One aspect of the present framework analyzes patient signal data using blood vessel mechanical signal data. The framework may non-invasively acquire mechanical signal data (e.g., vibration, acoustic signal data, etc.) generated by mechanical contraction of blood vessels caused by the heart from remote parts of the patient's body (e.g., wrist). The framework may quantitatively characterize such mechanical signal data to sensitively detect cardiac tissue function distortion and arrhythmia pathologies. By precise diagnosis of patterns of blood vessel mechanical signal data, the framework provides an efficient, accurate and reliable method for diagnosing cardiac function and healthy status, identifying cardiac disorders, characterizing pathological severities, predicting life-threatening events, evaluating drug intervention effects, and other clinical applications. These and other exemplary features and advantages will be described in the following.

FIG. 1 shows an exemplary system 100 for implementing a method and system of the present disclosure. It is to be understood that, because some of the constituent system components and method steps depicted in the accompanying figures can be implemented in software, the actual connections between the system components (or the method steps) may differ depending upon the manner in which the present framework is programmed. For example, the system 100 may be implemented in a client-server, peer-to-peer (P2P) or master/slave configuration. In such configurations, the system 100 may be communicatively coupled to other systems or components via a network, such as an Intranet, a local area network (LAN), a wide area network (WAN), a P2P network, a global computer network (e.g., Internet), a wireless communication network, or any combination thereof. Given the teachings of the present invention provided herein, one of ordinary skill in the related art will be able to contemplate these and similar implementations or configurations of the present invention.

As shown in FIG. 1, the system 100 may include a computer system 101 and a sensor system 130. The computer system 101 may include, inter alia, a central processing unit (CPU) or processor device 102, a non-transitory computer-readable media 105, one or more output devices 111 (e.g., printer, display monitor, projector, speaker, etc.), a network controller 103, an internal bus 106 and one or more input devices 108, for example, a keyboard, mouse, touch screen, gesture and/or voice recognition module, etc. Computer system 101 may further include support circuits such as a cache, a power supply, clock circuits and a communication bus. Various other peripheral devices, such as additional data storage devices and printing devices, may also be connected to the computer system 101.

The present technology may be implemented in various forms of hardware, software, firmware, special purpose processors, or a combination thereof, either as part of a microinstruction code or as part of an application program or software product, or a combination thereof, which is executed via the operating system. In one implementation, the techniques described herein may be implemented as computer-readable program code tangibly embodied in non-transitory computer-readable media 105. Non-transitory computer-readable media or memory device 105 may include random access memory (RAM), read only memory (ROM), magnetic floppy disk, flash memory, and other types of memories, or a combination thereof. The present techniques may be implemented by patient signal analysis unit 122 that is stored in computer-readable media 105. As such, the computer system 101 is a general-purpose computer system that becomes a specific-purpose computer system when executing the computer-readable program code.

The same or different computer-readable media 105 may be used for storing a database 124. Database 124 may include a repository of determined parameters, indices and/or ratios, selectable predetermined functions, patient signal data (e.g., vibration, acoustic, shaking, electrophysiological, ECG, intra-cardiac electrograms (ICEG), respiration signal data, hemodynamic or vital sign data, etc.), patient data (e.g., demographic data, pathology history, etc.), other input data and/or other derived output parameters.

Patient signal data may be provided by a sensor system 130 that is communicatively coupled to the computer system 101 via a communication link 144. In some implementations, communication link 144 is wired data communication link. Alternatively, the communication link 144 may be a wireless data communication link established via wireless signal transmitter 142.

Sensor system 130 may be configured to be removably attachable to a site of a patient's body for non-invasive mechanical signal data acquisition. In some implementations, sensor system 130 is implemented as a wrist attachment (e.g., sports band, fitness band, hospital-specific monitoring band, wrap, watch, ring, etc.) that non-invasively acquires signal data from the patient's wrist. Sensor system 130 may include a sensor module (148, 150, 152), a signal digitization component (not shown) for digitizing the sensor data acquired by sensor module (148, 150, 152) and a data communications controller (not shown) (e.g., wired and/or wireless communications controller) for transferring the digitized sensor data to computer system 101. The sensor system 130 may further include an internal power supply (e.g., battery) or an interface device to receive power from an external power supply (e.g., wired interface or wireless power-voltage converter). In some implementations, one or more components (e.g., signal analysis unit 122) of computer system 101 are integrated with sensor system 130.

Sensor module may include different kinds of sensors, such as a pulse vibration sensor (or converter) 148, a mechanical acoustic sensor (or converter) 150 and an optical sensor 152. Other types of sensors, such as a shaking sensor, may also be incorporated. Each sensor may be working independently, or synchronized and gated by different synchronization signals to provide multiple sensor signal data. Synchronization signals may be provided by other sensors in the sensor module or derived from other patient signals, such as surface ECG signals, blood pressure, SPO2 signal, etc.

The sensor system 130 may non-invasively convert, digitize and transfer the digitized sensor data in real time to computer system 101 to perform real-time recording, monitoring and diagnosis. Optionally, an indicator may be incorporated in the sensor system 130 to provide, in substantially real time, patient status or warning to, for example, the doctor, nurse or patient. The indicator may include, for example, a light emitting diode (LED) indicator, display screen, speaker, buzzer, etc., to efficiently and timely warn the user of any detected cardiac pathology (e.g., arrhythmia trend, malfunction severity, etc.). In some implementations, the indicator is a display screen configured to display further information associated with the patient status or warning, such as a list of persons (e.g., doctors, nurses, hospital staff, etc.) who have been alerted, caregivers associated with the patient, waveforms of patient signals (e.g., normal and abnormal regions), functionalities to customize the view of the waveforms (e.g., zooming in, pan, etc.), and so forth. The data communications controller may be also be able to communicate with other medical devices, such as implantable cardiac defibrillator (ICD) system, anesthesia system, treatment devices (e.g. stimulation and ablation devices), etc.

Figure 2:
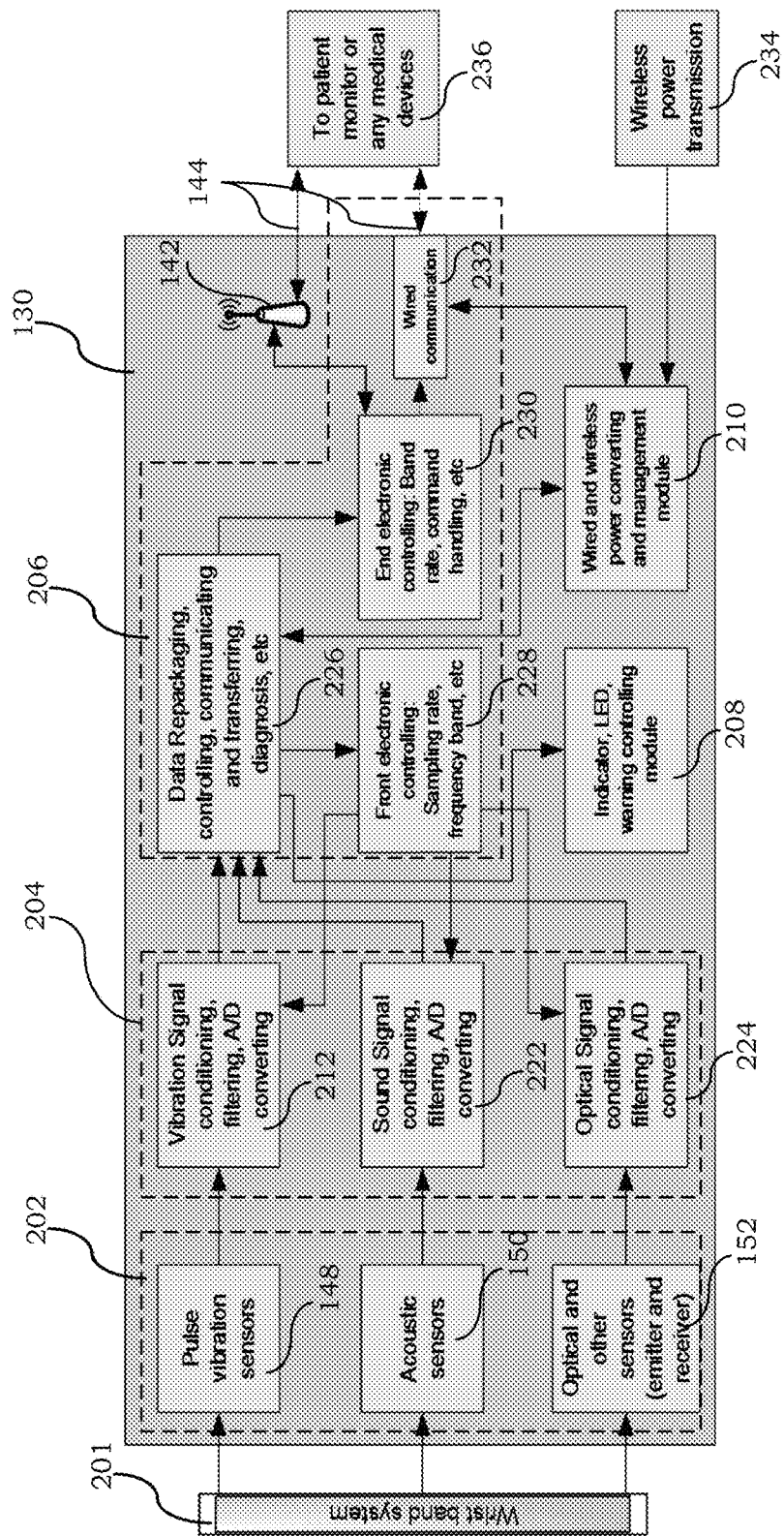
FIG. 2 shows an exemplary wristband sensor system.

FIG. 2 shows an exemplary wristband sensor system 130. Exemplary wristband sensor system 130 may monitor and record various types of blood flow acoustic and vibration signals, as well as other signals, which are originally caused by heart and can be remotely sensed at the wrist. Exemplary wristband sensor system 130 may further filter and convert the signal data to digital data series, package digitized data, perform diagnosis based on the digitized data to generate preliminary diagnostic results, transfer and/or display the preliminary diagnostic results and/or data to a patient monitor and/or other medical devices via wired and/or wireless transmission, and so forth.

In some implementations, the sensor system 130 includes a wristband system 201, sensor module 202, signal digitization component 204, central control module 206, indicator 208 and power supply interface 210. Wristband system 201 is a mechanical system configured to be removably attachable to a wrist. Wristband system 201 may include, for example, an elongated flexible band to wrap around the wrist of a patient. Sensor module 202 may include cardiac pulse vibration sensors 148, acoustic (or sound) sensors 150 for acquiring blood flow measurement data, optical sensor 152 for acquiring oximetric data and/or other sensors that include emitter and receiver. Signal digitization component 204 may include components for signal conditioning, controlled filtering (or frequency band selection) and analog to digital (A/D) conversion. Different sub-components 212, 222 and 224 may be provided to process vibration signal data, acoustic (or sound) signal data and optical signal data respectively.

Central control module 206 may include sub-module 226 for repackaging different kinds of digitized sensor data, controlling function and command, communicating and transferring data, determining preliminary diagnosis, and so forth. Central control module 206 may further include front and back end data communications controllers 228 and 230 for managing sampling rate, frequency bandwidth, band rate, handling commands, etc. to communicate data via wired communication link 232 or wireless transmitter 142 to the patient monitor 236 or any other medical device (e.g., computer system 101). Patient monitor 236 may be stationary in a room, mobile (e.g., tablet device or hospital cart), or implemented on or about the wristband for easy access when the patient is moved around the facility or hospital. Indicator 208 may provide LED indication, warning, etc. in response to cardiac diagnostic results generated by, for example, central control module 206 or computer system 101. Power supply interface 210 may convert wired and/or wireless power supplied by wireless power transmission 234 to provide power to the whole system 130.

Figure 3:
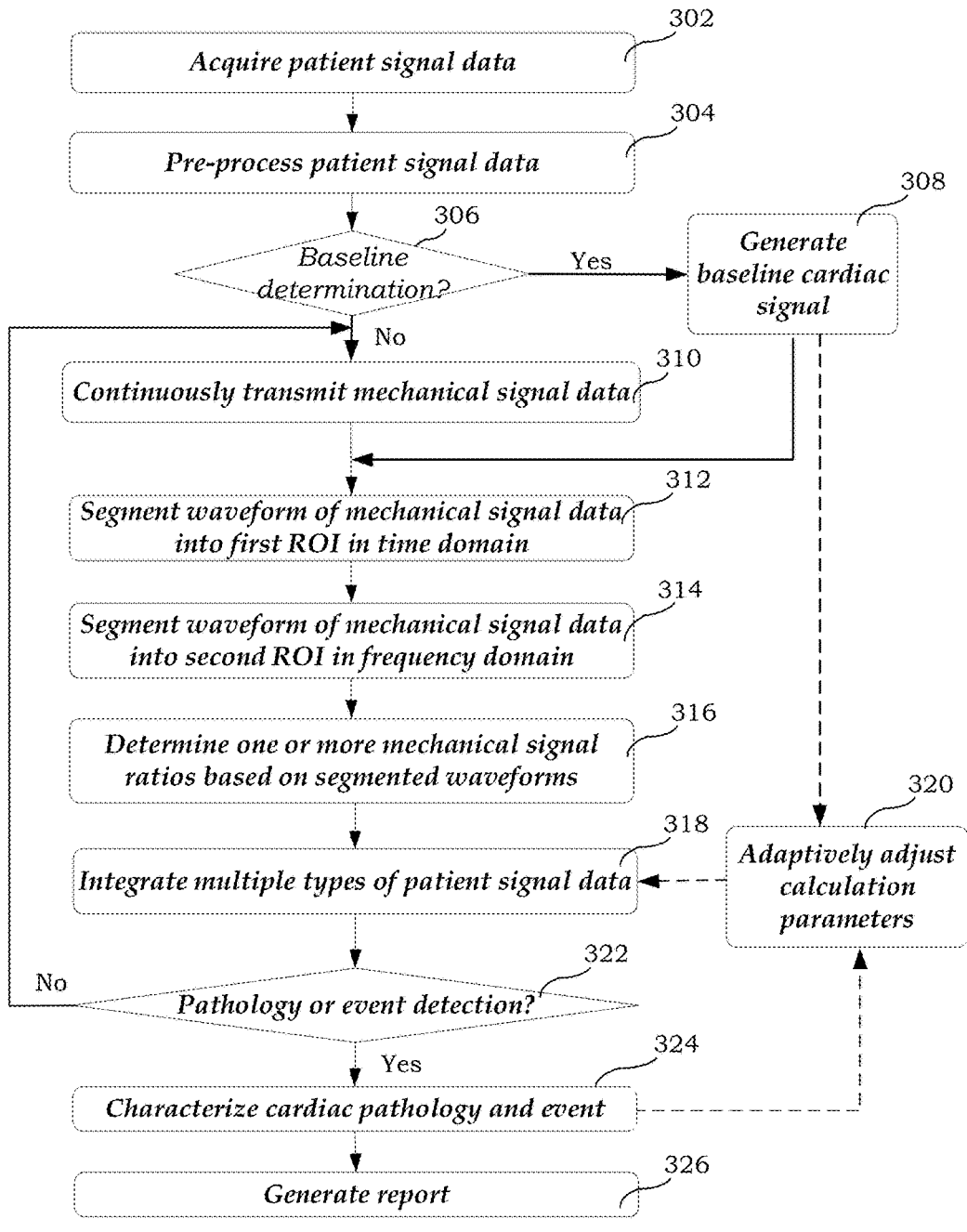
FIG. 3 shows an exemplary method of analyzing mechanical patient signal data.

FIG. 3 shows an exemplary method 300 of analyzing mechanical patient signal data. The steps of the method 300 may be performed in the order shown or a different order. Additional, different, or fewer steps may be provided. Further, the method 300 may be implemented with the system 100 of FIG. 1, system 130 of FIG. 2, a different system, or a combination thereof.

At 302, patient signal data is acquired. Such patient signal data may be represented by a waveform or graph with, for example, time represented on the x-axis and voltage or amplitude represented on the y-axis. Such patient signal data includes mechanical signal data that is non-invasively acquired from a site (e.g., wrist, finger, etc.) of a patient's body that is remote from the heart. Mechanical signal data include any type of signal data that is caused by the mechanical contraction of blood vessels, such as pulse vibration, blood flow acoustic, pulse shaking signal data, etc. Such mechanical signal data may be acquired by, for example, wristband sensor module 202 configured to be removably attached to the wrist, as previously described with reference to FIG. 2.

In some implementations, cardiac electrophysiological signal data, such as electrographic (ECG) data, surface ECG data, etc., are further acquired. Alternatively, or additionally, other types of electrophysiological signal data, such as hemodynamic (HEMO) signal data (e.g., invasive blood pressure (IBP), non-invasive blood pressure signal data, cardiac output signals, etc.), respiration (or capnographic) signal data, blood pressure data, oximetric (SPO2) data, capnographic signal data, temperature, and/or other vital sign signal data, other measurable patient biometric, physiological or medical signals, may also be acquired. In addition, other patient information, such as demographic data, clinical application and patient status, including, but not limited to, weight, height, gender, age, allergies, medications, pathology history, pathology treatment history, etc., may also be acquired.

At 304, the patient signal data is pre-processed. Signal digitization component 204 may pre-processes the patient signal data by conditioning, filtering, data conversion of patient signal data acquired by the sensor system 130, amplification, digitization and/or buffering. For example, the patient signal data may be pre-filtered and amplified for display on, for instance, computer system 101. The patient signal data may be filtered to remove unwanted patient movement and respiratory artifacts, as well as power line noise. The filter may be adaptively selected in response to data indicating clinical application (e.g. ischemia detection application, rhythm analysis application). The patient signal data may be conditioned, converted, amplified, buffered, filtered and/or digitized to produce a continuous stream of digitized samples.

At 306, central control module 206 determines whether a baseline is to be automatically extracted from the digitized mechanical signal data. The baseline cycle (or signal) generally refers to a known reference cycle (or benign signal) with which an unknown cycle (or value) is compared when measured or assessed. The baseline cycle may be used in, for example, threshold determination, computation of parameters or indices, calculation comparison, and so forth.

If the baseline is to be automatically determined, at 308, signal analysis unit 122 automatically generates the baseline cycle (or signal). The baseline may be adaptively adjusted according to the current application and clinical requirements. Alternatively, if the baseline is not to be automatically determined, the user may manually select it via, for example, a user interface.

At 310, central control module 206 continuously transmits patient signal data to the computer system 101 and/or other medical devices. Such data transmission may be wired or wireless.

At 312, patient signal analysis unit 122 segments the waveform of the patient signal data into a first region of interest (ROI) in the time domain. The first region of interest (ROI) may be any portion of the waveform that is identified for further analysis. The first region of interest may be, for example, one or more sound beats of the wrist pulse acoustic signal, or one or more vibration beats of the wrist blood flow vibration signal that corresponds to a cardiac cycle in the time domain.

Figure 4:
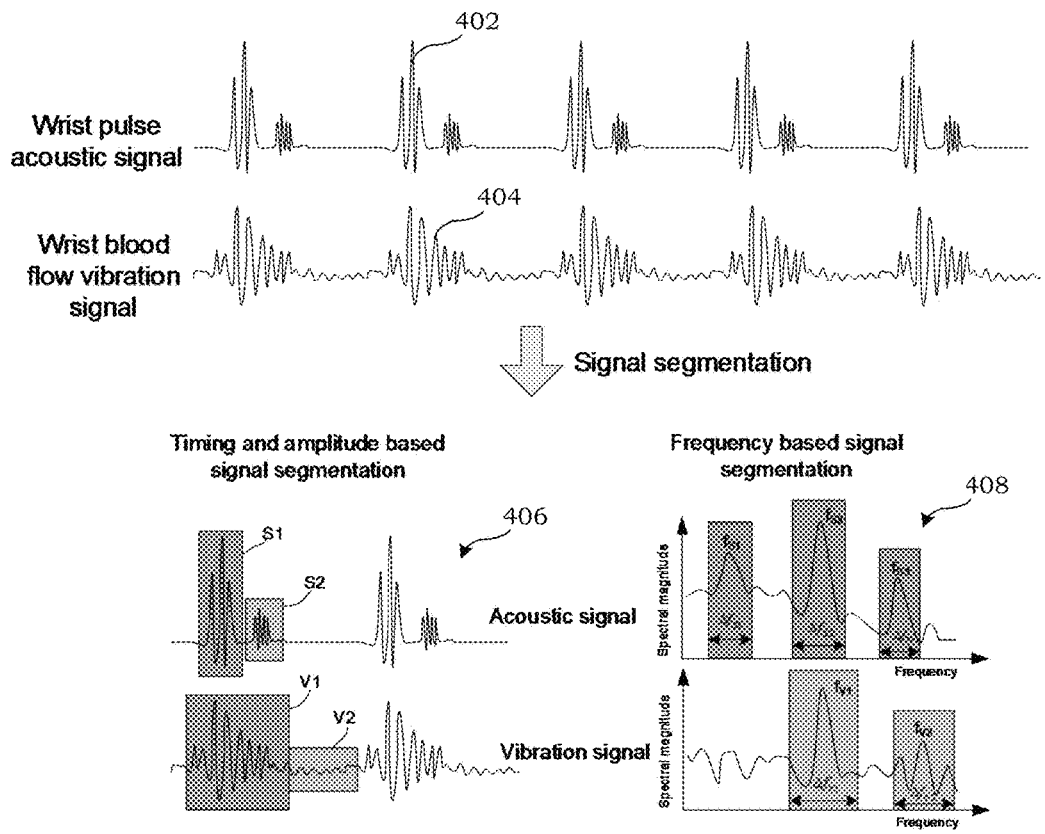
FIG. 4 illustrates exemplary methods for segmenting a wrist pulse acoustic signal and a wrist blood flow vibration signal.

FIG. 4 illustrates exemplary methods for segmenting a wrist pulse acoustic signal 402 and a wrist blood flow vibration signal 404. Based on the morphologies of the signal data (402 and 404), the shape and timing of the signal waveforms can be synchronized and gated with other patient signals (e.g., ECG or blood pressure signal cycles). The acoustic and vibration signals (402 and 404) may be segmented into different portions based on cardiac pulse functionality and mode, such as by timing (see 406) or frequency (see 408).

As illustrated by 406, a sound beat (which corresponds to a cardiac cycle) of the acoustic signal 402 may be separated into two portions (S1 and S2) based on signal activity density and energy. A beat of the vibration signal 404 may be segmented into two portions (V1 and V2) by cardiac signal vibration mode, such as contraction and rest. For example, 5% of the maximum amplitude of the beat waveform morphology may be used as a threshold for separating the different portions V1 and V2. Based on clinical application and user design preference, the threshold value may be adaptively adjusted.

Figure 5:
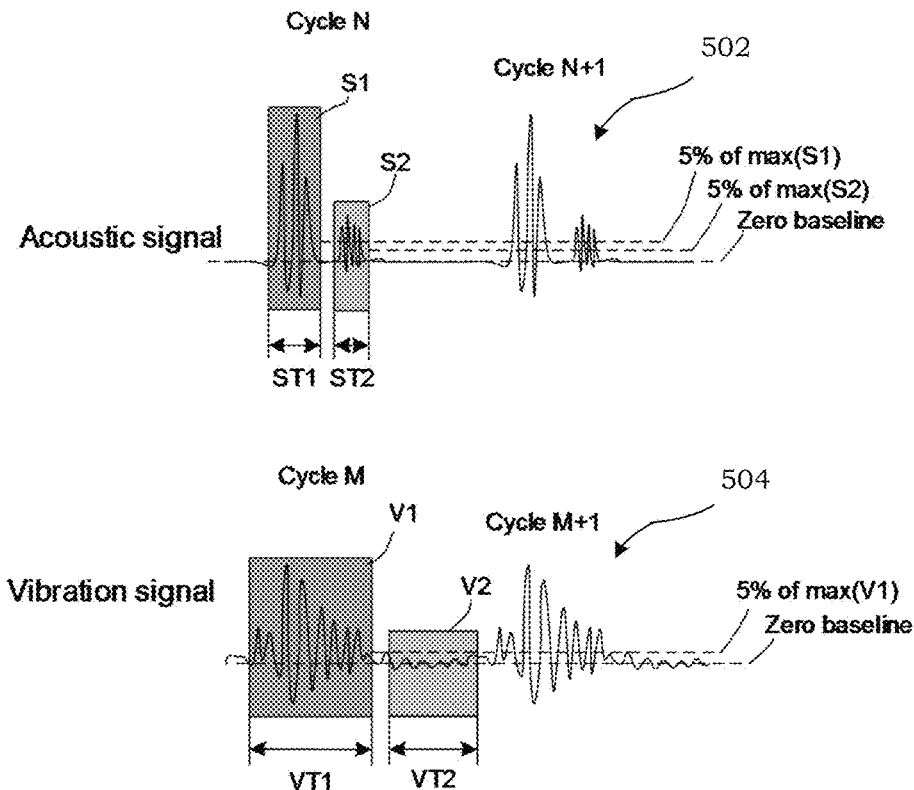
FIG. 5 shows a more detailed illustration of an exemplary segmentation of time domain acoustic and vibration signals.

FIG. 5 shows a more detailed illustration of an exemplary segmentation of time domain acoustic and vibration signals. The signals may be segmented into different ROI portions with different timing durations and thresholds for categorization. For example, referring to 502 for the acoustic signal, there are two significant sound portions. Accordingly, 5% of the first maximum signal amplitude and 5% of the second maximum signal amplitude are utilized as the amplitude or signal magnitude thresholds to identify S1 and S2 portions respectively. Referring to 504 for the vibration signal, 5% of the first maximum amplitude is used as the threshold in defining and separating the signal into portions V1 and V2. It should be appreciated that the threshold values for segmentation and identification of different ROI portions may be adaptively adjusted by clinical users or system 101. Parameters such as time durations ST1, ST2, VT1, VT2, etc. may be extracted from the segmented ROI portions to determine mechanical signal ratios or indices, as will be described later.

Returning to FIG. 3, at 314, patient signal analysis unit 122 segments the waveform of the patient signal data into a second region of interest (ROI) in the frequency domain. The second region of interest (ROI) may be any portion of the waveform that is identified for further analysis. The second region of interest may be, for example, one or more frequency components (or spectral amplitude and range) of the wrist pulse acoustic signal or the wrist blood flow vibration signal in the frequency domain that correspond to a cardiac cycle in the time domain. The cardiac cycle may be detected by, for example, detecting an R wave to R wave interval in the ECG signal.

Acoustic and vibration signals may be converted from the time domain into frequency domain. Different cardiac patients may have different intrinsic frequency range and dominant frequency peaks. For example, acoustic signal data may include, but is not limited to, three peak frequencies that are in frequency bands of 1-15 Hz, 20-60 Hz, and 150-200 Hz, while wrist pulse vibration signal data may include, but is not limited to, two obvious peak frequencies 1-10 Hz and 20-100 Hz. Other frequency bands or cardiac pulse signature ranges may also be used. Clinical users or system 101 may adaptively shift the corresponding dominant frequency peaks and ranges based on the clinical application and diagnosis needs.

As shown by 408 of FIG. 4, the wrist acoustic and vibration signals (402 and 404) may be categorized in the frequency domain. In some implementations, acoustic signal 402 is segmented into 3 portions corresponding to 3 frequency peaks ($f_{S1}$, $f_{S2}$, $f_{S3}$) and vibration signal 404 is segmented into 2 portions corresponding to 2 frequency peaks ($f_{V1}$, $f_{V2}$). Parameters extracted from the ROI portions, such as frequency peaks and corresponding ROI frequency ranges ($\Delta f_{S1}$, $\Delta f_{S2}$, $\Delta f_{S3}$, $\Delta f_{V1}$, $\Delta f_{V2}$), may be utilized as frequency signatures of cardiac rhythms for cardiac pulse mode and pattern characterization (e.g., dominant frequency peak values, dominant frequency ratios, energy ratios, etc.), as will be described later.

At 316, patient signal analysis unit 122 determines one or more mechanical signal ratios based on parameters extracted from the segmented waveforms to characterize changes in the signal data waveform. Such mechanical signal ratios may include a unipolar ratio or a bipolar ratio. A unipolar ratio compares parameters extracted from different ROI portions within the same cardiac cycle (or wrist pulse cycle), while a bipolar ratio compares parameters extracted from ROI portions of different cardiac cycles (or wrist pulse cycles). Unipolar ratios may include, but are not limited to, unipolar time ratios, unipolar time integration ratios, unipolar time energy integration ratios, unipolar dominant frequency ratios, unipolar frequency energy integration ratios, and so forth. Bipolar ratios may include, but are not limited to, bipolar time ratios, bipolar time integration ratios, bipolar time energy integration ratios, bipolar dominant frequency ratios, bipolar frequency energy integration ratios, and so forth. In the following discussion, reference may be made to components illustrated by FIGS. 4 and 5.

In some implementations, unipolar time ratios are determined to compare time durations extracted from portions of the region of interest. Unipolar time ratios may be determined as follows:

$$\text{Uni\_time\_ratio}_{Sound}(N) = \frac{ST1}{ST2} \quad (1)$$

$$\text{Uni\_time\_ratio}_{Vibration}(M) = \frac{VT1}{VT2} \quad (2)$$

wherein Uni_time_ratio$_{Sound}$(N) and Uni_time_ratio$_{Vibration}$(M) denote unipolar time ratios for sound cycle N and vibration cycle M respectively; ST1 and ST2 are time durations of ROI portions for sound cycle N; and VT1 and VT2 are time durations of the ROI portions for vibration cycle M.

In some implementations, unipolar time integration ratios are determined to compare time domain magnitudes of portions of the region of interest. Unipolar time integration ratios may be determined based on the following:

$$\text{Uni\_time\_integration\_ratio}_{Sound}(N) = \frac{\int_{i \in ST1} a(i)}{\int_{j \in ST2} a(j)} \quad (3)$$

$$\text{Uni\_time\_integration\_ratio}_{Vibration}(M) = \frac{\int_{p \in VT1} b(p)}{\int_{q \in VT2} b(q)} \quad (4)$$

wherein Uni_time_integration_ratio$_{Sound}$(N) and Uni_time_integration_ratio$_{Vibration}$(M) denote unipolar time integration ratios for sound cycle N and vibration cycle M respectively; ST1 and ST2 are time intervals of the ROI portions for sound cycle N; and VT1 and VT2 are time intervals of ROI portions for vibration cycle M; a(i) and a(j) are time domain magnitudes of the acoustic signal waveform at time points i and j; and b(p) and b(q) are time domain magnitudes of the vibration signal waveform at time points p and q.

In some implementations, unipolar time energy integration ratios are determined to compare time domain magnitudes of portions of the region of interest. Unipolar time energy integration ratios may be determined based on the following:

$$\text{Uni\_time\_energy\_integration\_ratio}_{Sound}(N) = \frac{\int_{i \in ST1} |a(i)|^2}{\int_{j \in ST2} |a(j)|^2} \quad (5)$$

$$\text{Uni\_time\_energy\_integration\_ratio}_{Vibration}(M) = \frac{\int_{p \in VT1} |b(p)|^2}{\int_{q \in VT2} |b(q)|^2} \quad (6)$$

wherein Uni_time_energy_integration_ratio$_{Sound}$(N) and Uni_time_energy_integration_ratio$_{Vibration}$(M) denote unipolar time energy integration ratios for sound cycle N and vibration cycle M respectively; ST1 and ST2 are time intervals of ROI portions for sound cycle N; VT1 and VT2 are time intervals of ROI portions for vibration cycle M; a(i) and a(j) are time domain magnitudes of the acoustic signal waveform at time points i and j; and b(p) and b(q) are time domain magnitudes of vibration signal waveform at time points p and q.

As discussed previously, each of the sound and vibration pulse cycle signals can be converted into frequency domain waveforms, which can be used to calculate and diagnose the mode and pattern of cardiac function and events. In the frequency domain, different peak frequencies are defined as dominant frequency peaks indicative of the principal frequency components and signal spectral concentration.

In some implementations, unipolar dominant frequency ratios are determined to compare dominant peak frequency values of portions of the region of interest. Unipolar dominant frequency ratios may be determined based on the following:

$$\text{Uni\_dominant\_frequency\_ratio}_{Sound}(N) = \frac{f_{Si}}{f_{Sj}} \quad (7)$$

$$\text{Uni\_dominant\_frequency\_ratio}_{Vibration}(M) = \frac{f_{Vp}}{f_{Vq}} \quad (8)$$

wherein Uni_dominant_frequency_ratio$_{Sound}$(N) and Uni_dominant_frequency_ratio$_{Vibration}$(M) denote unipolar frequency ratios for sound pulse cycle N and vibration pulse cycle M respectively; $f_{Si}$ and $f_{Sj}$ are dominant peak frequency values of corresponding ROI portions for sound cycle N; $f_{Vp}$ and $f_{Vq}$ are dominant frequency peak values of corresponding ROI portions for vibration cycle M; Si and Sj are frequency peaks of the frequency spectrum derived from the acoustic signal; and Vp and Vq are frequency peaks of the frequency spectrum derived from the vibration signal.

In some implementations, unipolar frequency energy integration ratios are determined to compare frequency spectral magnitudes of portions of the region of interest. Unipolar frequency energy integration ratios are determined based on the following:

$$\text{Uni\_frequency\_energy\_integration\_ratio}_{Sound}(N) = \frac{\int_{m \in \Delta f_{Si}} |A(f_m)|^2}{\int_{n \in \Delta f_{Sj}} |A(f_n)|^2} \quad (9)$$

$$\text{Uni\_frequency\_energy\_integration\_ratio}_{Vibration}(M) = \frac{\int_{m \in \Delta f_{Vi}} |A(f_m)|^2}{\int_{n \in \Delta f_{Vj}} |A(f_n)|^2} \quad (10)$$

wherein Uni_frequency_energy_integration_ratio$_{Sound}$(N) and Uni_frequency_energy_integration_ratio$_{Vibration}$(M) denote unipolar frequency energy integration ratios for sound pulse cycle N and vibration pulse cycle M respectively; A(●) represents the spectral magnitude of the corresponding frequency ROI portion in a dominant bandwidth for acoustic or vibration signal; $f_m$ and $f_n$ denote discrete frequency points for integration calculation; $\Delta f_{Si}$ and $\Delta f_{Sj}$ denote frequency durations of ROI dominant frequency bandwidths for the acoustic signal; and $\Delta f_{Vi}$ and $\Delta f_{Vj}$ are frequency durations of ROI dominant frequency bandwidths for the vibration signal.

Different combinations of parameters extracted from different cardiac cycles may be used to derive cross or mutual information between cycles for cardiac rhythm and function diagnosis. Such cross or mutual information may be represented by bipolar ratios, such as cross or mutual ratios. In the following description, N and M denote ongoing real time acquired pulse cycles, while N+1 and M+1 denote subsequent cardiac cycles or predetermined cardiac cycles for use as index or data comparison. The ratio between same ROI portions of different cardiac cycles are herein referred to as mutual ratios, such as S1(N) versus S1(M) for acoustic signals and V1(N) versus V1(M) for vibration signals, wherein N and M denote different cardiac cycles. The ratio between different ROI portions of different cardiac cycles are herein referred to as cross ratios, such as S1(N) versus S2(M) for acoustic signals and V1(N) versus V2(M) for vibration signals, wherein N and M denote different cardiac cycles. To simplify the definitions, the following description integrates the definition in equations with different parameter indices: if the indices of the comparison are the same, it is a mutual bipolar ratio; otherwise, it is cross bipolar ratio.

In some implementations, bipolar time ratios are determined to compare time durations extracted from portions of the region of interest. Bipolar time ratios may be determined as follows:

$$\text{Bi\_time\_ratio}_{Sound}(N) = \frac{STi(N)}{STj(N+1)} \quad (11)$$

$$\text{Bi\_time\_ratio}_{Vibration}(M) = \frac{VTi(M)}{VTj(M+1)} \quad (12)$$

wherein Bi_time_ratio$_{Sound}$(N) and Bi_time_ratio$_{Vibration}$(M) denote bipolar time ratios for sound cycle N versus cycle N+1 and vibration cycle M versus cycle M+1; STi(N) and STi(N+1) are time durations of ST ROI portion i in sound cycle N and ST ROI portion j in sound cycle N+1; and VTi(M) and VTi(M+1) are time durations of VT ROI portion i in sound cycle M and VT ROI portion j in sound cycle M+1. If i=j, it is referred to as a mutual time ratio between two cardiac cycles; if i≠j, it is referred to as a cross time ratio between two cardiac cycles.

In some implementations, bipolar time integration ratios are determined to compare time domain magnitudes of portions of the region of interest. Bipolar time integration ratios may be determined based on the following:

$$\text{Bi\_time\_integration\_ratio}_{Sound}(N) = \frac{\int_{m \in STi(N)} a(m)}{\int_{n \in STj(N+1)} a(n)} \quad (13)$$

$$\text{Bi\_time\_integration\_ratio}_{Vibration}(M) = \frac{\int_{p \in VTi(M)} b(p)}{\int_{q \in VTj(M+1)} b(q)} \quad (14)$$

wherein Bi_time_integration_ratio$_{Sound}$(N) and Bi_time_integration_ratio$_{Vibration}$(M) denote bipolar time integration ratios for sound cycle N versus cycle N+1 and vibration cycle M versus cycle M+1; STi(N) and STi(N+1) are time intervals of #i ST ROI portion in sound cycle N and #j ST ROI portion in sound cycle N+1; and VTi(M) and VTi(M+1) are time intervals of #i VT ROI portion in sound cycle M and #j VT ROI portion in sound cycle M+1; a(m) and a(n) are time domain magnitudes of the acoustic signal waveform at time points m and n; and b(p) and b(q) are time domain magnitudes of the vibration signal waveform at time points p and q. When i=j, it is referred to as a mutual time ratio between two cardiac cycles; when i≠j, it is referred to as a cross time ratio between two cardiac cycles.

In some implementations, bipolar time energy integration ratios are determined to compare time domain magnitudes of portions of the region of interest. Bipolar time energy integration ratios may be determined based on the following:

$$\text{Bi\_time\_energy\_integration\_ratio}_{Sound}(N) = \frac{\int_{m \in STi(N)} |a(m)|^2}{\int_{n \in STj(N+1)} |a(n)|^2} \quad (15)$$

$$\text{Bi\_time\_energy\_integration\_ratio}_{Vibration}(M) = \frac{\int_{p \in VTi(M)} |b(p)|^2}{\int_{q \in VTj(M+1)} |b(q)|^2} \quad (16)$$

wherein Bi_time_energy_integration_ratio$_{Sound}$(N) and Bi_time_energy_integration_ratio$_{Vibration}$(M) denote bipolar time energy integration ratios for sound cycle N versus cycle N+1 and vibration cycle M versus cycle M+1; STi(N) and STi(N+1) are time intervals of #i ST ROI portion in sound cycle N and #j ST ROI portion in sound cycle N+1; and VTi(M) and VTi(M+1) are time intervals of #i VT ROI portion in sound cycle M and #j VT ROI portion in sound cycle M+1; a(m) and a(n) are time domain magnitudes of the acoustic signal waveform at time points m and n; and b(p) and b(q) are time domain magnitudes of the vibration signal waveform at time points p and q. When i=j, it is referred to as a mutual time ratio between two cardiac cycles; when i≠j, it is referred to as a cross time ratio between two cardiac cycles.

In some implementations, bipolar dominant frequency ratios are determined to compare dominant peak frequency values of portions of the region of interest. Bipolar dominant frequency ratios may be determined based on the following:

$$\text{Bi\_dominant\_frequency\_ratio}_{Sound}(N) = \frac{f_{Si}(N)}{f_{Sj}(N+1)} \quad (17)$$

$$\text{Bi\_dominant\_frequency\_ratio}_{Vibration}(M) = \frac{f_{Vp}(M)}{f_{Vq}(M+1)} \quad (18)$$

wherein Bi_dominant_frequency_ratio$_{Sound}$(N) and Bi_dominant_frequency_ratio$_{Vibration}$(M) denote bipolar frequency ratios for sound pulse cycle N versus sound pulse cycle N+1 and vibration pulse cycle M versus vibration pulse cycle M+1; $f_{Si}$(N) and $f_{Sj}$(N+1) are dominant frequency peak values of selected corresponding ROI portions of frequency waveform for sound cycle N and sound cycle N+1; and $f_{Vp}$(M) and $f_{Vq}$(M+1) are dominant frequency peak values of selected corresponding ROI portions of frequency waveform for vibration cycle M and cycle M+1; Si and Sj are frequency peaks of the acoustic frequency spectral in different sound cycles; Vp and Vq are frequency peaks of the vibration frequency spectral in different vibration cycle. When i=j, it is referred to as a mutual time ratio between two pulse cycles; when i≠j, it is referred to as a cross time ratio between two cardiac cycles.

In some implementations, bipolar frequency energy integration ratios are determined to compare frequency spectral magnitudes of portions of the region of interest. Bipolar frequency energy integration ratios are determined based on the following:

$$\text{Bi\_frequency\_energy\_integration\_ratio}_{Sound}(N) = \frac{\int_{m \in \Delta f_{Si}(N)} |A(f_m)|^2}{\int_{n \in \Delta f_{Sj}(N+1)} |A(f_n)|^2} \quad (19)$$

-continued $$\text{Bi\_frequency\_energy\_integration\_ratio}_{Vibration}(M) = \frac{\int_{m \in \Delta f_{V_i}(M)} |A(f_m)|^2}{\int_{n \in \Delta f_{V_j}(M+1)} |A(f_n)|^2} \quad (20)$$

wherein Bi_frequency_energy_integration_ratio$_{Sound}$(N) and Bi_frequency_energy_integration_ratio$_{Vibration}$(M) denote bipolar frequency energy integration ratios for sound pulse cycle N versus sound pulse cycle N+1 and vibration pulse cycle M versus vibration pulse cycle M+1; A(●) is the magnitude of corresponding frequency ROI portion in sound or vibration dominant frequency peak bands; $f_m$ and $f_n$ are discrete frequency points for integration calculation; $\Delta f_{Si}$(N) and $\Delta f_{Sj}$(N+1) are selected frequency durations of the ROI dominant frequency bands for sound signal in cycle N and cycle N+1; $\Delta f_{Vi}$(M) and $\Delta f_{Vj}$(M+1) are selected frequency durations of the ROI dominant frequency bands for vibration signal in cycle M and cycle M+1; Si and Sj are peaks of the sound frequency spectral in different sound cycles; Vi and Vj are peaks of the vibration frequency spectral in different vibration cycles. When i=j, it is referred to as a mutual time ratio between two cardiac cycles; when i≠j, it is referred to as a cross time ratio between two cardiac cycles.

At 318, patient signal analysis unit 122 integrates different types of patient data, including parameters, ratios and/or indices generated by the present framework. Although each index, ratio and/or defined parameter generated by the present framework may be independently utilized to monitor patient healthy status based on cardiac or wrist pulse mode (or pattern), accuracy and reliability may be improved by combining different indices, parameters and/or ratios.

In some implementations, an artificial neural network (ANN) is used for nonlinear data information fusion of different kinds of patient data. By using multi-channel and multiple kinds of patient signal data (when available), such as different lead ECG NIBP, SPO2 signals, etc., cardiac arrhythmia may be more efficiently detected and characterized. For example, cardiac disorders may be identified, cardiac arrhythmias may be differentiated, pathological severities may be characterized, life-threatening events may be predicted, and drug delivery and effects may be evaluated.

Figure 6:
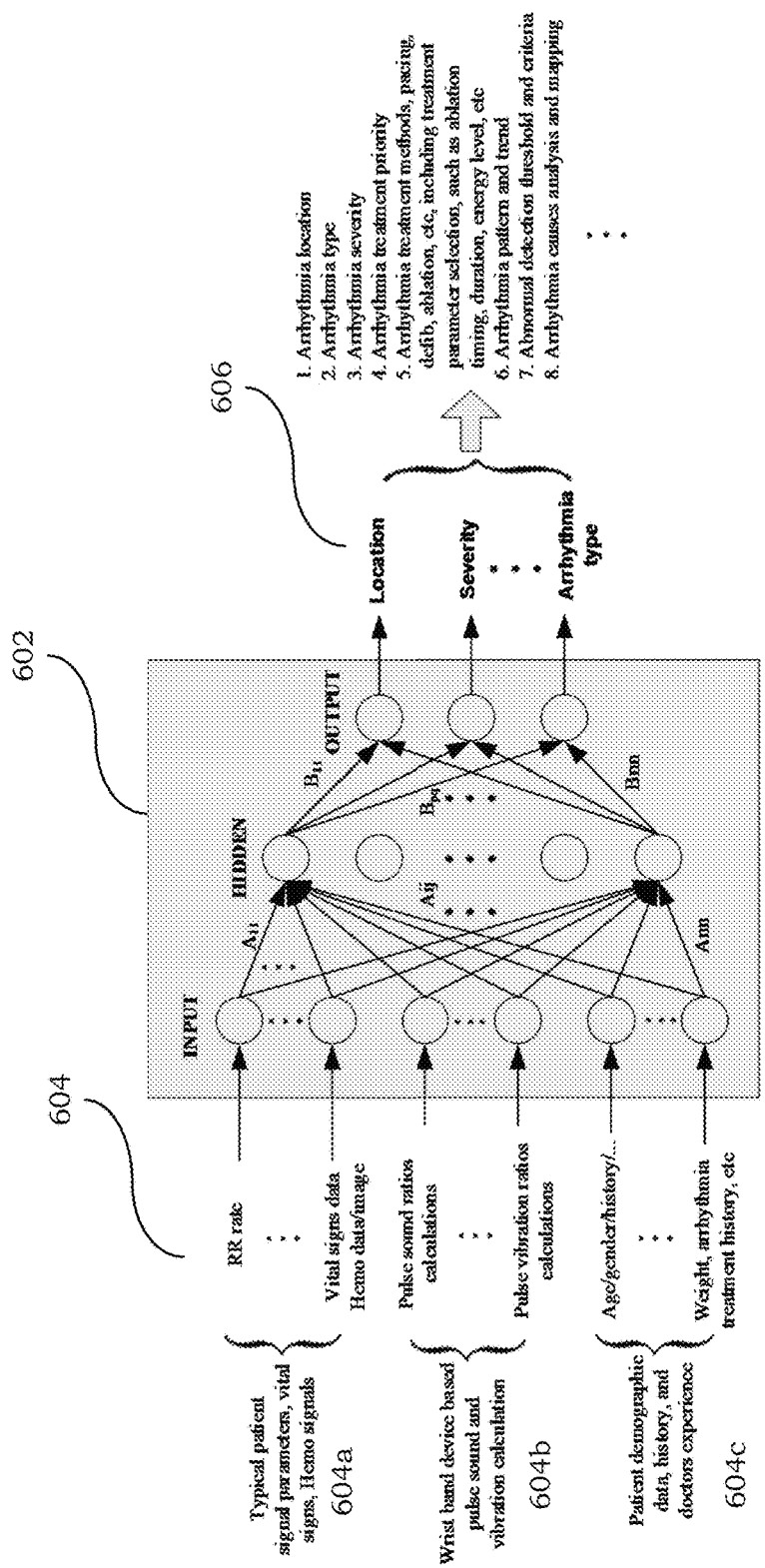
FIG. 6 shows an exemplary artificial neural network (ANN) module for multi-data fusion.

FIG. 6 shows an exemplary artificial neural network (ANN) module 602 for multi-data fusion. There are 3 layers in the ANN module 602: input layer, hidden layer and output layer. $A_{ij}$ denote weights between the input layer and the hidden layer, while $B_{pq}$ denote weights between the hidden layer and the output layer. The weights $A_{ij}$ and $B_{pq}$ can be adaptively adjusted with training data set.

The ANN module 602 has self-learning capability with new input data 604, which can increase the accuracy of calculated results 606. The ANN module 602 combines typical signal parameters and vital sign data 604a, patient signal analysis results (e.g., pulse sound time and frequency domain ratios, pulse vibration time and frequency domain ratios, etc.) 604b generated by the present framework, and patient data, history and doctor's knowledge 604c to generate output results 606 for detecting and treating emerging pathological events and arrhythmia. More detailed patient status and treatment parameters 606 can be derived, via the ANN module 602, for achieving optimized cardiac rhythm management (CRM). Exemplary output parameters 606 include, but are not limited to, cardiac arrhythmia type, severity, location, time stamp, event trend, treatment parameter and suggestions (e.g., treatment location, priority, treatment method and control parameters, etc.). By using multi-channel signal data and multiple kinds of patient data, cardiac arrhythmia can be more efficiently detected and characterized.

Returning to FIG. 3, at 320, patient signal analysis unit 122 may optionally adaptively adjust calculation parameters used for calculating the aforementioned parameters, ratios and/or indices. The adaptive adjustment may be performed automatically, semi-automatically or manually by the clinical user based on clinical experience and knowledge. Such calculation parameters may include, but are not limited to, calculation window size, signal portion, ROI area, time steps, severity thresholds, and so forth. The framework may include a hypothesis test, such as T test, etc., for determining calculation parameters such as detection threshold and criteria. Such calculation parameters may be re-input into the ANN module 602 so as to improve stability and sensitivity (true positive and false positive rate) of the output diagnosis and characterization.

At 322, patient signal analysis unit 122 determines if pathology or cardiac event detection is to be performed. If not, the method 300 returns to step 310. If yes, the method 300 proceeds to next step 324.

At 324, patient signal analysis unit 122 characterizes the cardiac pathology and event. Such characterization may be achieved using an ANN module, such as ANN module 602 previously described with reference to FIG. 6.

At 326, patient signal analysis unit 122 generates a patient report. The patient report may present the abnormality, associated characteristics (e.g., location, type, severity, timing, etc.) and other information (e.g., suggested treatment options). The patient report may be in the form of, for example, an alert message, warning or indicator. The patient report may also be stored in database 124 for future retrieval, transmitted or shared with other client computers, and/or printed in physical form for viewing.

Figure 7:
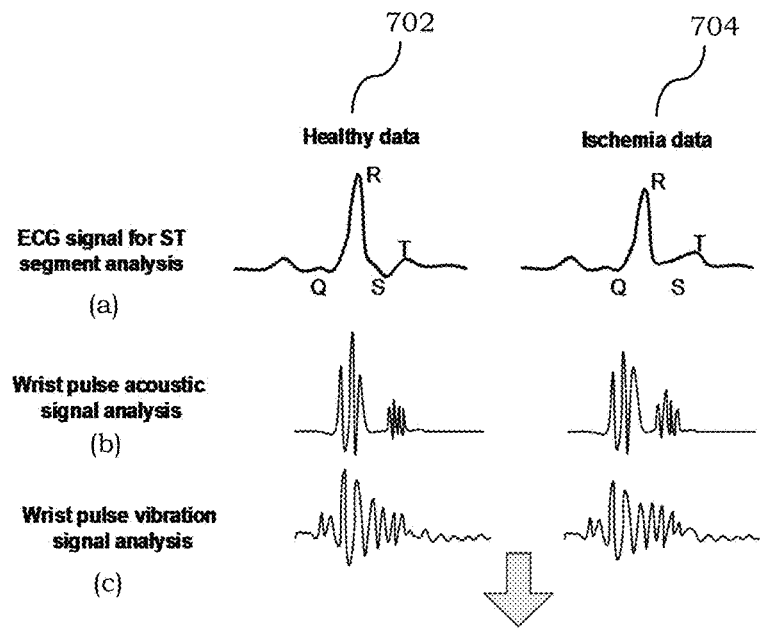
FIG. 7 shows an exemplary computer simulation.

FIG. 7 shows an exemplary computer simulation that generates results using an exemplary cardiac sound and vibration ratio analysis for myocardial ischemia event (as provided by the present framework) and a gold clinical standard ST segment analysis. The gold standard ST segment analysis is a conventional technique that detects heart myocardial ischemia by using ST segment portion voltage displacements to quantify the myocardial ischemia event, such as 0.1 mV elevation. However, ST segment voltage changes typically cannot be used to characterize severity and detect ischemia events and pathologies.

In the example shown in FIG. 7, three methods were used to compare diagnoses for a normal (or healthy) event 702 and a myocardial ischemia (or arrhythmia) event 704. The three methods are: (a) Gold standard ST segment analysis; (b) wrist pulse acoustic signal analysis; and (c) wrist pulse vibration signal analysis. Comparing two cardiac signal episodes, normal case and early ischemia case, ST segment could detect the early myocardial ischemia event in 25 seconds, while wrist pulse acoustic signal and wrist pulse vibration signal analyses could detect the early ischemia event in 5 and 5.5 seconds respectively. The detection threshold was set to 25% of the reference signal comparison index. If using the same time stamp (10 seconds in the example herein), the ST segment elevation was only 0.03 mV, while acoustic and vibration signal ratio indices changed by 35% and 33% respectively. This example illustrates the sensitivity of the wrist pulse acoustic and vibration signal analyses. If additional ratios and/or indices are generated with the ANN module, the analysis may be even more sensitive and reliable.

While the present invention has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

The invention claimed is:

1. A system for patient signal analysis, comprising:
a sensor system including sensors that non-invasively acquire at least first and second types of mechanical signal data from a patient, wherein the at least first and second types of mechanical signal data is generated in response to contraction of blood vessels; and
a computer system communicatively coupled to the sensor system, wherein the sensor system is configured to continuously and wirelessly transmits the first and second types of mechanical signal data to the computer system, wherein the computer system includes
a non-transitory memory device for storing computer readable program code, and
a processor in communication with the memory device, the processor being operative with the computer readable program code to perform steps including
segmenting a first region of interest from each of the first and second types of mechanical signal data into first and second different portions by using a predetermined percentage of first and second maximum amplitudes of the mechanical signal data, wherein the first region of interest corresponds to a cardiac cycle,
determining first and second mechanical signal ratios based on first and second parameters extracted from the first and second portions of the first and second types of mechanical signal data, wherein the first and second mechanical signal ratios characterize waveform changes, wherein the first mechanical signal ratio comprises a time integration ratio of an integral of time domain magnitudes of the first portion to an integral of time domain magnitudes of the second portion,
determining a third mechanical signal ratio comprising a frequency energy integration ratio that compares integrals of frequency spectral magnitudes of first and second portions of a second region of interest of the mechanical signal data in a frequency domain,
integrating, via an artificial neural network, at least the first, second and third mechanical signal ratios to generate output results for detecting a cardiac pathology, and
generating a report based at least in part on the output results.

2. The system of claim 1 wherein the sensor system is configured to be removably attachable to a wrist.

3. The system of claim 1 wherein the one or more sensors comprise a pulse vibration sensor and the mechanical signal data comprises vibration signal data.

4. The system of claim 1 wherein the one or more sensors comprise an acoustic sensor and the mechanical signal data comprises acoustic signal data.

5. The system of claim 1 wherein the one or more sensors comprise an optical sensor and the mechanical signal data comprises oximetric signal data.

6. The system of claim 1 wherein the sensor system further comprises an indicator that provides warning of a detected cardiac pathology.

7. A method of patient signal analysis, comprising:
continuously and wirelessly receiving, by a processor device from a sensor system, patient signal data including at least first and second types of mechanical signal data generated in response to contraction of blood vessels;
segmenting, by the processor device, a first region of interest from each of the first and second types of mechanical signal data into first and second different portions by using a predetermined percentage of first and second maximum amplitudes of the mechanical signal data, wherein the first region of interest corresponds to a cardiac cycle;
determining, by the processor device, first and second mechanical signal ratios based on first and second parameters extracted from the first and second portions of the first and second types of mechanical signal data, wherein the first and second mechanical signal ratios characterize waveform changes, wherein the first mechanical signal ratio comprises a time integration ratio of an integral of time domain magnitudes of the first portion to an integral of time domain magnitudes of the second portion;
determining, by the processor device, a third mechanical signal ratio comprising a frequency energy integration ratio that compares integrals of frequency spectral magnitudes of first and second portions of a second region of interest of the mechanical signal data in a frequency domain;
integrating, via an artificial neural network, at least the first, second and third mechanical signal ratios to generate output results for detecting a cardiac pathology; and
generating, by the processor device, a report based at least in part on the output results.

8. The method of claim 7 wherein determining the first and second mechanical signal ratios comprises determining one or more ratios of a first value to a second value, wherein the first value is determined based on a first parameter extracted from the first portion and the second value is determined based on a second parameter extracted from the second portion.

9. The method of claim 7 further comprising extracting time durations from the first region of interest to generate the first mechanical signal ratio.

10. The method of claim 7 wherein the frequency energy integration ratio comprises a unipolar ratio that compares parameters extracted from portions in a same cardiac cycle.

11. The method of claim 7 further comprising:
extracting frequency peaks from the first and second portions of the second region of interest; and
determining a fourth mechanical signal ratio of a first value to a second value, wherein the first value is derived based on the frequency peak from the first portion of the second region of interest and the second value is derived based on the frequency peak from the second portion of the second region of interest.

12. The method of claim 11 wherein determining the fourth mechanical signal ratio comprises determining a dominant frequency ratio that compares dominant peak frequency values of the first and second portions of the second region of interest.

13. The method of claim 7 wherein determining the first mechanical signal ratio comprises determining a unipolar ratio that compares parameters extracted from portions in a same cardiac cycle.

14. The method of claim 7 wherein determining the first mechanical signal ratio comprises determining a bipolar ratio that compares parameters extracted from portions in different cardiac cycles.

15. The method of claim 7 wherein determining the second mechanical signal ratio comprises determining a mutual ratio that compares parameters extracted from same portions in different cardiac cycles.

16. The method of claim 7 wherein determining the second mechanical signal ratio comprises determining a cross ratio that compares parameters extracted from different portions in different cardiac cycles.

17. The method of claim 7 wherein determining the second mechanical signal ratio comprises determining a time ratio that compares time durations of the first and second portions of the first region of interest.

18. The method of claim 7 wherein the frequency energy integration ratio comprises a bipolar ratio that compares parameters extracted from portions in different cardiac cycles.

19. A non-transitory computer readable medium embodying a program of instructions executable by machine to perform steps for patient signal analysis, the steps comprising:

continuously and wirelessly receiving, by a processor device from a sensor system, patient signal data including at least first and second types of mechanical signal data generated in response to contraction of blood vessels;

segmenting, by the processor device, a first region of interest from each of the first and second types of mechanical signal data into first and second different portions by using a predetermined percentage of first and second maximum amplitudes of the mechanical signal data, wherein the first region of interest corresponds to a cardiac cycle;

determining, by the processor device, first and second mechanical signal ratios based on first and second parameters extracted from the first and second portions of the first and second types of mechanical signal data, wherein the first and second mechanical signal ratios characterize waveform changes, wherein the first mechanical signal ratio comprises a time integration ratio of an integral of time domain magnitudes of the first portion to an integral of time domain magnitudes of the second portion;

determining, by the processor device, a third mechanical signal ratio comprising a frequency energy integration ratio that compares integrals of frequency spectral magnitudes of first and second portions of a second region of interest of the mechanical signal data in a frequency domain;

integrating, via an artificial neural network, at least the first, second and third mechanical signal ratios to generate output results for detecting a cardiac pathology; and generating, by the processor device, a report based at least in part on the output results.

\* \* \* \* \*